United States Patent
Irion et al.

(10) Patent No.: US 6,212,425 B1
(45) Date of Patent: Apr. 3, 2001

(54) APPARATUS FOR PHOTODYNAMIC DIAGNOSIS

(75) Inventors: Klaus Irion, Emmingen-Liptingen; Reinhold Baumgartner, Freising; Herbert Stepp, Planegg; André Ehrhardt, Tuttlingen, all of (DE); Karlheinz Strobl, Fiskdale, MA (US)

(73) Assignee: Karl Storz GmbH & Co., KG (DE)

( * ) Notice: Subject to any disclaimer, the term of this patent is extended or adjusted under 35 U.S.C. 154(b) by 0 days.

(21) Appl. No.: 09/043,850

(22) PCT Filed: Sep. 26, 1996

(86) PCT No.: PCT/DE96/01831

§ 371 Date: Sep. 18, 1998

§ 102(e) Date: Sep. 18, 1998

(87) PCT Pub. No.: WO97/11636

PCT Pub. Date: Apr. 3, 1997

(30) Foreign Application Priority Data

Sep. 26, 1995 (DE) .............................. 195 35 829
Dec. 31, 1995 (DE) .............................. 195 48 913

(51) Int. Cl.[7] ........................................ A61B 5/00

(52) U.S. Cl. .................................................. 600/476

(58) Field of Search .................... 600/312, 317, 600/321, 329, 476, 478

(56) References Cited

U.S. PATENT DOCUMENTS 4,768,513 * 9/1988 Suzuki ................................. 600/476
5,590,660 * 1/1997 MacAulay ............................ 600/478

* cited by examiner

Primary Examiner—William E. Kamm
(74) Attorney, Agent, or Firm—St. Onge Steward Johnston & Reens LLC (57) ABSTRACT

A device for "in vivo" diagnosis by means of a photosensibilisator light-induced reaction or a reaction caused by intrinsic fluorescence in biological tissue, having an illumination system, which is provided with at least one light source having a lamp system which generates incoherent light in a wavelength range of at least 380 to 680 nm, a light delivering unit which directs the light of said illumination system at the therapy and/or to-be-diagnosed tissue area, and an imaging, image-recording and image-transmitting unit which images the light coming from said tissue area in a proximal image plane. The device is distinguished in that the net spectral transmittance in the light delivering unit and in the image-generating unit of the device are selected in such a manner that, on the one hand, practically no light with a wavelength of $\lambda$ from the range utilized for excitation, which by nature has relatively high intensity, "reaches" via the image-generating unit of the device into the proximal image plane, whereas light with a wavelength of $\lambda$ from the range in which fluorescence occurs can reach the proximal image plane only if it comes from the illuminated tissue are and not from the illumination system.

86 Claims, 5 Drawing Sheets

APPARATUS FOR PHOTODYNAMIC DIAGNOSIS

DESCRIPTION

1. Technical Field

The present invention relates to a device for "in vivo diagnosis" by means of an intrinsic or foreign photosensibilisator light-induced reaction in biological tissue.

2. State of the Art

The method of diagnosis performed with a device of this type is also referred to in medicine as photodynamic diagnosis (PDD) or as fluorescence diagnosis. Moreover, using photosensibilisators for photodynamic therapy (PDT) is also known. With regard to this see WO 93/20810 to which, moreover, reference is explicitly made for the explanation of all terms and process steps not explained more closely herein.

Furthermore, it has been proposed to perform endoscopic photodynamic diagnosis and therapy using a device which utilizes a Krypton ion laser with a wavelength of approximately 410 nm and power of more than 200 mWatt as the light source. The light of this laser is guided via a quartz light conductor having a small numerical aperture through an endoscope to the to-be-irradiated sites of the human body.

In order to trigger a light-induced reaction in biological systems, the patient is given a photosensibilisator, which either has a hematoporphyrin basic structure such as the substance photofrin and photosan-3, or delta amino levulinic acid (ALA), recently in use in urology and dermatology, in a concentration of few mg/kg body weight. The hematoporphyrin derivatives are dispensed intravenously, whereas delta amino levulinic acid can be applied locally, i.e. it is injected as a solution, by way of illustration, into the urinary bladder. These substances accumulate in tumor tissues in double to ten-fold concentrations. This selective accumulation in tumor tissue represents a decisive basis for photodynamic diagnosis and photodynamic therapy.

For diagnosis, the to-be-examined tissue is irradiated endoscopically with violet light, in known devices practically solely laser light, approximately 2–12 hours following dispensing the photosensibilisator (ALA). The porphyrin derivatives, high concentrations of which are present in the tumor tissue, are excited by this light and subsequently have a typical red fluorescence, by means of which the tumor can be localized.

In addition to fluorescence, due to the accumulation of the photosensibilisator in the tissue, so-called autofluorescence of the tissue may be triggered due to so-called fluorophorene, i.e. intrinsic fluorescence substances.

In photodynamic therapy, irradiation is conducted with red light, because this light with a wavelength of more than 630 nm penetrates the tissue to a depth of about 5 mm contrary to light with shorter wavelengths, which penetrates strikingly less deep. Despite the use of this optimum wavelength, the indication for use of photodynamic therapy is presently limited to flat, surface carcinoma.

It can be assumed the biological course of the light-induced reaction is as follows:

The photosensiblisator stored in the tissue is excited by the absorption of a light quantum with a defined energy content emitted by the respective light source. If violet light is irradiated within the scope of the photodynamic diagnosis, fluorescence radiation is emitted upon returning to the initial state.

If photodynamic therapy occurs in conjunction with radiation using red laser light of higher power density, there is a transition from the excited state to a metastabilized intermediate state, from which the energy which is released by the return to the initial state is transmitted to the molecular oxygen, which absorbs this energy forming excited singulet oxygen. This aggressive singulet oxygen destroys the cell structures in the concerned tissue by means of photooxidation. This cellular damage in conjunction with the simultaneous collapse of the tumor vessel system leads to complete destruction of the tumor (phototoxic effect).

However, this procedure has certain problems depending on the photosensibilators employed. If photofrin and photosan-3 are used as photosensibilisators for photodynamic diagnosis, technologically very complicated devices have to be employed for fluorescence detection, because due to the interfering intrinsic-fluorescence, the fluorescence of the tumor tissue can only be suitably detected with the aid of very complicated, computer-supported image processing technology and highly sensitive cameras with low-light amplifiers.

If delta amino levulinic acid is utilized, the induced fluorescence is strong enough that it can be visibly recognized. However, the fluorescence obtained with the delta amino levulinic acid does not yield an optimum quality endoscopic image for recording for the diagnosis. The use of a quartz light conductor with a small numerical aperture, such as is employed for light transmission of a laser beam, permits only very poor illumination of the image.

Employing an additional light conductor, which could improve illumination, reduces the lumen available for the other channels in the endoscope to such an extent that it drastically decreases the possibility of utilizing other endoscopic instruments.

Above all, when using known devices, the additional light introduced into the endoscope may superimpose the, even with delta amino levulinic acid, relatively weak fluorescence image.

Moreover, the aforedescribed processes for the diagnosis and therapy require different light sources, and in particular laser sources, which, on the one hand, increases costs and, on the other hand, makes handling the endoscopic system more difficult.

Similar problems arise when conducting photodynamic diagnosis using a microscope and, in particular using a surgical microscopic.

SUMMARY OF THE INVENTION

The object of the present invention is to improve a device for diagnosis by means of an intrinsic or foreign photosensibilisator light-induced reaction or a reaction caused by intrinsic fluorescence in biological tissue in such a manner that the induced fluorescence can be detected with a strong contrast while at the same time there being sufficient illumination, preferably not using lasers, for observing the tissue area.

The solutions of the object of the present invention are based on the following fundamental concept:

The net transmittance in the light delivering part and in the image-generating part of the invented device are selected in such a manner that, on the one hand, practically no light with a wavelength of $\lambda$ from the range used for excitation, which by nature has relatively high intensity, "reaches" via the image-generating part of the device into the proximal image plane, whereas light with a wavelength of $\lambda$ from the range in which fluorescence occurs can only reach the proximal image plane if it comes from the illuminated area of tissue and not from the illumination system. On the other hand, the net transmittance of the light delivering part and of the image-generating part of the device ensures that the illuminated area of tissue is so strongly illuminated with light of a wavelength which lies neither in the range of the excitation spectrum nor in the range of the fluorescence spectrum, that the examining individual can perceive, due to this wavelength range of the directly reflected light, details of the illuminated area of tissue independent of the fluorescence radiation.

In other words, an element of the present invention is that the image of the tissue area illuminated with excited light is simultaneously generated by means of fluorescence light and reflected illumination light, with the two portions contributing to image generation are of such a nature with regard to wavelength and with regard to their intensity that they do not "interfere" with each other.

The invented device for diagnosis by means of a light-induced reaction in biological tissue by means of an intrinsic or foreign photosensibilisator respectively by means of intrinsic fluorescence is provided with an illumination system having at least one light source, a light delivering unit which directs the light of the illumination system at the to-be-diagnosed area of tissue and an imaging unit which images the light coming from the tissue in a proximal image plane. Devices for diagnosis of corporal tissue having the aforementioned features are commonly known and are used, by way of illustration, in endoscopy or microscopy.

An element of the present invention is that, a wide band light source is employed, in a manner, as such, known outside photodynamic diagnosis, which emits incoherent light in a wavelength range of at least 380 to 660 nm, preferably from 370 to 780 nm. This wide band light source may possess a different spectral distribution than that of conventional light sources used in endoscopy. However, if the light source is also utilized for conventional examination of the area examined with photodynamic diagnosis as well, it is preferable if the light source is a conventional high-power light source like those used in medical endoscopy. The power input of the light source is preferably at least 300 watt.

When using "wide band" light sources, in the past the problem arose that the light reflected at the to-be-examined area of tissue superimposes the fluorescence light. For this reason, an element of the present invention is that not only the net transmittance $Ti_1(\lambda)$ of the light delivering unit is adapted to the fluorescence excitation spectrum of the photosensibilisator and the net transmittance $Ti_b(\lambda)$ of the imaging unit to the fluorescence spectrum of the photosensibilisators.

Alternatively an element of the present invention is that, the net transmittance of the entire system comprising the light delivering unit and the imaging unit, yielded by the multiplication of net transmittance $Ti_l(\lambda)$ and $Ti_b(\lambda)$, has a spectral transmittance of more than 5% only in a range of a maximum of 50 nm and is otherwise less than 5%. In this range of a maximum of 50 nm, the net transmittance of the entire system may attain values of 10% and more.

In the alternative, the net spectral transmittance $Ti_l(\lambda)$ of the light delivering unit has, in addition to a first pass region, which is adapted to that of the fluorescence excitation spectrum of the photosensibilisator respectively of the tissue, also a second pass region, the wavelengths of which lie between the wavelengths of the fluorescence excitation spectrum and the wavelengths of the fluorescence spectrum. The net spectral transmittance $Ti_b(\lambda)$ of the imaging unit has, in addition to a first pass region, which is adapted to the fluorescence spectrum of the photosensibilisator respectively of the tissue, also a second pass region which lies in the same wavelength range as that of the second pass region of the light delivering unit. The net transmittance of the entire system comprising the light delivering unit and the imaging unit has a spectral transmittance of more than 5%, which preferably may be 10% and more, only in the second pass region and is otherwise less than 5% in the above wavelength range.

As a result of this design of the spectral pass regions of the light delivering unit and of the imaging unit, the fluorescence light can be perceived clearly and with a strong contrast on the image generated by the illumination light by way of illustration of the surroundings of a tumor.

It is preferred if the first and the second pass regions of the imaging unit are approximately complementary, yielding a strong contrast between the fluorescence image and the illuminated background image, which contrast can be enhanced by an alternating representation of both images on a monitor.

Furthermore, it is preferred if the intensity of the illumination light and the filters are selected in such a manner that the power input of the light with wavelengths from the second range arriving on the proximal image plane is 10% (and less)up to approximately 100% of the cumulated power of the light in the first pass region of the imaging unit.

In order to adapt the different photosensibilisators and/or different diagnostic conditions or in order to convert the invented device to a therapeutic procedure, it is furthermore preferred if the transmission properties of the light transmitting unit and of the imaging unit can be adjusted by means of one or multiple optical elements.

It is preferred if the setting occurs in such a manner that the intensity of the induced fluorescence light lies in the same magnitude as the overall intensity of the reflected part of the light of the illumination system. Especially advantageous is if the setting occurs in such a manner that both intensities are approximately the same.

In any case, the invented device has the advantage that in order to conduct photodynamic diagnosis while at the same time illuminating the observed field and for preliminary and/or follow-up visual observation of the examined area, it suffices to employ a single light source. Furthermore, the photodynamic therapy can be performed with the invented device without changing the light source, i.e. with a single light source. In this event, as previously mentioned, the transmission properties of the light delivering unit are adapted to the absorption spectrum of the photosensibilisator.

The optical elements employed for adjusting the transmission properties of the light delivering unit and of the imaging unit are preferably filter systems which can be placed in the illumination beam path and in the examination beam path. The illumination beam path refers to the beam path of the lamp of the light source to the light delivering unit, via this unit and from this unit to the area of tissue to be diagnosed. The optical elements and, in particular, the filter systems can principally be disposed in any site of this beam path. However, especially preferred is the arrangement between the illumination system and the light delivering unit, by way of illustration a light-conducting fiber bundle. (Without a filter system, the net transmittance is assumed 100%.)

Accordingly, the observation beam path refers to the beam path from the illuminated area of tissue to the imaging unit and from there to the proximal image plane. (Without a filter system the net transmittance is also assumed 100%.

If the invented device is integrated in an endoscope, the image plane can be located in the endoscope both in the region of the distal end, by way of illustration when using a distally disposed video chip, as well as in the region of the proximal end. In the latter case, the imaging unit has, in addition to a lens as an imaging unit, for example, a relay lens system or a flexible fiber bundle as the image transmitting unit. If a relay lens system or a fiber bundle are employed as the image transmitting unit, the filter systems placed in the observation beam path are preferably disposed between the "last surface" of the relay lens system respectively of the exit surface of the fiber bundle and the proximal image plane.

If the invented device is integrated in a surgical microscope, a component of the imaging unit is the microscope lens system downstream of which, by way of illustration a video recorder can be disposed as the image recording unit.

As previously explained, an element of the present invention is that the illumination light reflected by the to-be-diagnosed area of tissue and its surrounding area does not superimpose the fluorescence light. In order to realize this inventive fundamental concept, it is preferred if the respective filter systems to be placed in the illumination beam path and in the observation beam path have practically opposite filter characteristics. In the case of a device designed according to claim 2, the opposite design of the filter characteristic relates, of course, only to the characteristic of the first pass region, but not to the characteristic of the second pass region.

The curves, showing the transmission of the two opposite filters in dependence on the wavelength, intersect, in the embodiment according to claim 1 preferably with a transmission of the individual systems which is less than 50%.

In another embodiment of the present invention, the filter placed in the illumination beam path is provided with at least two separate filters of which one filter is a thermostable interference filter and the other filter a thermostable heat protection filter (neutral filter).

In the following, the properties of these filters are explained under the precondition that delta amino levulinic acid is employed as the photosensibilisator. If another photosensiblisator is employed, the filter properties have to be adapted accordingly:

If delta amino levulinic acid (ALA) is used, it is preferable if the transmission of the illumination beam path by means of a short pass filter is at least 50% in the range between 380 and 430 nm. In an especially preferred embodiment, transmission between 370 and 440 nm is at least 70% and preferably 95%.

If the wavelength is 445±4 nm respectively 447±2 nm, transmission reaches 50%. In the event of greater wavelengths, transmission is much smaller and usually lies below 1%.

In a preferred embodiment of the present invention, transmission lies below 1% in the wave length range between 460 and 600 nm as well as in the wavelength range between 720, preferably 660 nm, and 780 nm. In the wavelength range in which mainly fluorescence light is excited, thus in the case of delta amino levulinic acid in the wavelength range between 600 and 720, preferably 660 nm, transmission is less than 0.1%.

These characteristic, of the filter system yields a light distribution of the illumination light which ensures that in the wavelength range in which mainly fluorescence light occurs, practically no "non-fluorescence light" is radiated back by the tissue area to be examined.

Accordingly, the filter in the observation beam path (long pass filter) has the following characteristic:

$T_f(\lambda=370–430 \text{ nm})<0.1\%$ $T_f(\lambda=453\pm2 \text{ nm})=50\%$ $T_f(\lambda=500–1100 \text{ nm})=95\%$, preferably 98–99%

The tolerance for the wavelengths of the two filters, at which the respective transmission is 50%, is preferably ±2 nm. This design of the filter ensures that the net transmission of the entire system is only in the range between 430 and 460 nm greater than 5%. The maximum value reached in this range should preferably not be more than 15%.

The use of optical elements and, in particular, of filters for influencing the radiation beam path transmission characteristic has the advantage that, by way of illustration, normal white-light illumination and observation can occur by swinging out the filter so that the examining person, thus by way of illustration a physician, can also assess the tissue area examined using fluorescence diagnosis, i.a. according to color. Color is, by way of illustration in the field of ophthalmology, an essential assessment criteria.

The thermostable heat protection filter (neutral filter) also employed in a preferred embodiment of the present invention, can have the following characteristic:

$T_f(\lambda=370–440 \text{ nm})>95\%$ $T_f(\lambda=440–700 \text{ nm})\approx90\%$ $T_f(\lambda=700 \text{ nm})=50\%$, $T_f(\lambda=720–1100 \text{ nm})<1\%$, The use of a thermostable heat protection filter has the advantage that the interference filter is not heated by infrared light during diagnosis. This heating could, under circumstances, alter the filter characteristic and reduce the sensitivity of a camera recording element as well as destroy the light transmitting unit due to the high intensity.

In any case, it is preferable if the individual filters are only placed upon need in the respective beam paths, with their removal from the beam path, under circumstances, being permitted or prevented by a monitoring signal.

As filters, commercially available filters provided, in accordance with the invention, with the "almost stepped-shaped" characteristic, thus by way of illustration known interference filters, can be provided the carrier material of which is quartz.

As the light source, known light sources can be employed as well, in particular, light sources known from endoscopy, which emit wide band in the mentioned wavelength range. A light source of this type, which emits light in sufficient intensity, is by way of illustration a gas discharge lamp and, in particular a xenon gas discharge high pressure lamp. Should in an individual case, the light output of the light source not suffice, a "pulsed" light source, such as a flash device or a laser, can be employed in addition to a "continuously operating" light source. Especially in the alternative solution set forth in claim 2, the light with a wavelength $\lambda$ in the first pass region can be generated with a laser, which may be a pulsed or a continuous wave laser. The light with wavelengths from the second pass region can then come from a more or less wide band "white light source".

Commercially available light conductors having at least one fiber which advantageously possesses a numerical aperture of more than 0.45 can be employed as the light transmitting units, especially in endoscopic uses, because efficient light conduction to the to-be-diagnosed area then becomes possible. Fibers of this type have, by way of illustration, a core of quartz and an encasing of a thermostable material.

In the event a light conducting fiber is employed, it is preferable if the light source, i.e. by way of illustration the gas discharge lamp, has a focal spot with a diameter of less than 2 mm, which is generated by an elliptical reflector, which has a numerical aperture for a light emergence of more than 0.45. In this case, highly efficient coupling between the illumination system and the light transmitting unit, thus the fiber light conductor is obtained.

Furthermore, a gas discharge lamp, whose focal spot is focused on a diameter of less than 2 mm by means of a parabolic reflector and a focus unit, can also be used. The focus unit is in this case preferably a lens system which has at least one element having an aspherical surface.

In another preferred embodiment of the present invention, the illumination system, thus the light source and optical elements connected upstream of the light source, such as filters, etc., is designed in such a manner that the excitation wavelengths are provided variable according to the respective, utilized photosensibilisator and the respective tissue to be diagnosed. This variability can either occur by corresponding influencing of the light source or by means of filters connected upstream, such as, e.g. graded filters or prisms.

In this manner, different areas of tissue can be selectively excited to fluorescence.

The invented device permits both visual observation of fluorescence and recording the fluorescence image with an image recorder, such as a video camera or the like.

This video camera respectively unit is disposed in the image plane of the imaging unit. In the event of distal disposal of the video unit, it is disposed in the image plane of the lens of the endoscope. In the event of proximal disposal of the video unit, it is disposed in the image plane of the image transmitting unit, thus of the relay lens system or of the fiber bundle. Alternatively, the video unit can be designed in such a manner that it records the eyepiece image. If a microscope is employed as the imaging unit, the video unit is disposed in such a manner that it records the eyepiece image of the surgical microscope.

The video unit can, in particular (at least), be provided with a CCD recorder. In this event, the gas discharge lamp may be a periodically operating flash discharge lamp which is triggered by a control and evaluation unit in such a manner that the flash exposure occurs solely in the light integration phase of the CCD recorder(s). In this way, highly effective illumination of the area to be examined is attained while reducing the application of light energy on the illumination system and on the surroundings, thereby also decreasing the heat respectively thermal load on the components.

If visual observation of the area to be examined should occur simultaneously or the light power input should be increased simultaneously, it is advantageous if, in addition, a continuously operating light source is provided.

In order to control the video signal, it is furthermore preferable if the video unit is provided with a variable exposure setting; in this way, video image superimposition can be prevented and a well-contrasted image is always obtained permitting good detection of the fluorescence radiation.

An invented device, which possesses the aforedescribed features, permits visual observation of the fluorescence image by means of the naked eye or by means of a video unit. However, a special advantage of the invented device is that the image generated by it permits largely automated evaluation:

For this purpose the output signal from the video unit is applied to an image processing system. This image processing system can execute a number of manipulations in the image delivered by the video unit:

Color images can, by way of illustration, be recorded via the RGB (red, yellow, blue) input channels and transformed into the HSI color space:

(H=Hue)

(S=Saturation)

(I=Intensity)

In the HSI space, the "fluorescence radiation", by way of illustration, caused by the tumors stands out due to HSI separation.

Furthermore, the image processing system can electronically fade out a hue range in the depicted color image to enhance the contrast between different areas. If the image processing system conducts RGB recording, the, by way of illustration, in addition blue and/or green channel can be switched on and off. This method has the advantage that switching off the blue and/or green channels lets the fluorescence image emerge particularly clearly.

This clear emergence is intensified by the image processing system fading the faded out color channel shutterlike into the color image, by way of illustration, represented on a monitor, yielding the viewer a "striking" representation, which particularly simplifies detection of tumors.

An examination procedure can occur approximately as follows:

First the tissue area is examined visually. In other words, a physician observes the area illuminated with "white" light with the eyepiece of an endoscope respectively of a microscope or on a monitor. In order to switch to photodynamic diagnosis, a short pass filter and, if need be, the thermostable heat protection filter is swung into the illumination beam path by means of a foot switch or a switch on the video camera. Simultaneously, the green channel and/or the blue channel are periodically switched off. In this way, the physician sees on the monitor once only the fluorescence image (or the "normal" image) and then the superimposition of the fluorescence image with the "normal" image, which is generated by the light from a small area in which the transmission of the entire system is not equal to 0, thus either the overlapping region or the second pass region. Reversely, the background image (blue channel) can also be periodically superimposed with the fluorescence image.

Furthermore, the imaging processing system can calculate the fluorescence contrast value at individual points of the image for the maximum fluorescence wavelength for determining possible tumors. If delta amino levulinic acid (ALA) is employed as the photosensibilisator, the contrast relationship of the wavelength of 630 nm to the intensity in the range of maximum 50 nm can be calculated, in which range the entire system has a spectral transmittance of more than 5%:

By comparing the images recorded with and without fluorescence excitation, in the easiest case subtraction of the images, the image processing unit can determine the intensity of the fluorescence radiation and can calculate the contrast, thereby permitting exact localization of possible tumors.

The invented device can be utilized for a great variety of medical examinations:

In addition to the especially preferred use in endoscopic applications, the invented device can also be employed in combination with a surgical microscope, by way of illustration, in neurosurgery, colposcopy of ophthalmology.

However, in any event, a device is yielded which possesses, in particular, the following advantages due to the joint observation of the illumination light reflected at the tissue simultaneously or alternating with the fluorescence light:

Orientation also of fluorescence negative tissue is possible.

The orientation realized according to the present invention has the advantage over solely white light illumination, in particular, if ALA is employed as the photosensibilisator that there is a strong emphasis of the vessel structure and clear visibility is yielded even if there is diffuse bleeding into the rinsing fluid.

The threshold value function of the blue light suppresses the non-specific red fluorescence of the normal tissue.

Above all, however, the detection of real fluorescence positive areas by means of color contrast is possible and not by means of intensity contrast, as would be the case if the illumination light were totally blocked. This simplifies, in particular, image processing!

The color contrast obtained according to the present invention, contrary to intensity contrast, is independent of the observation distance and of the observation angle, thereby reducing the possibility of error substantially. Moreover, complex image processing procedures are obviated so that in the event of automated detection simple image processing procedures can be used.

BRIEF DESCRIPTION OF THE DRAWING

The present invention is made more apparent in the following using preferred embodiments with reference to the drawing, showing in.

DESCRIPTION OF PREFERRED EMBODIMENTS

Figure 1:
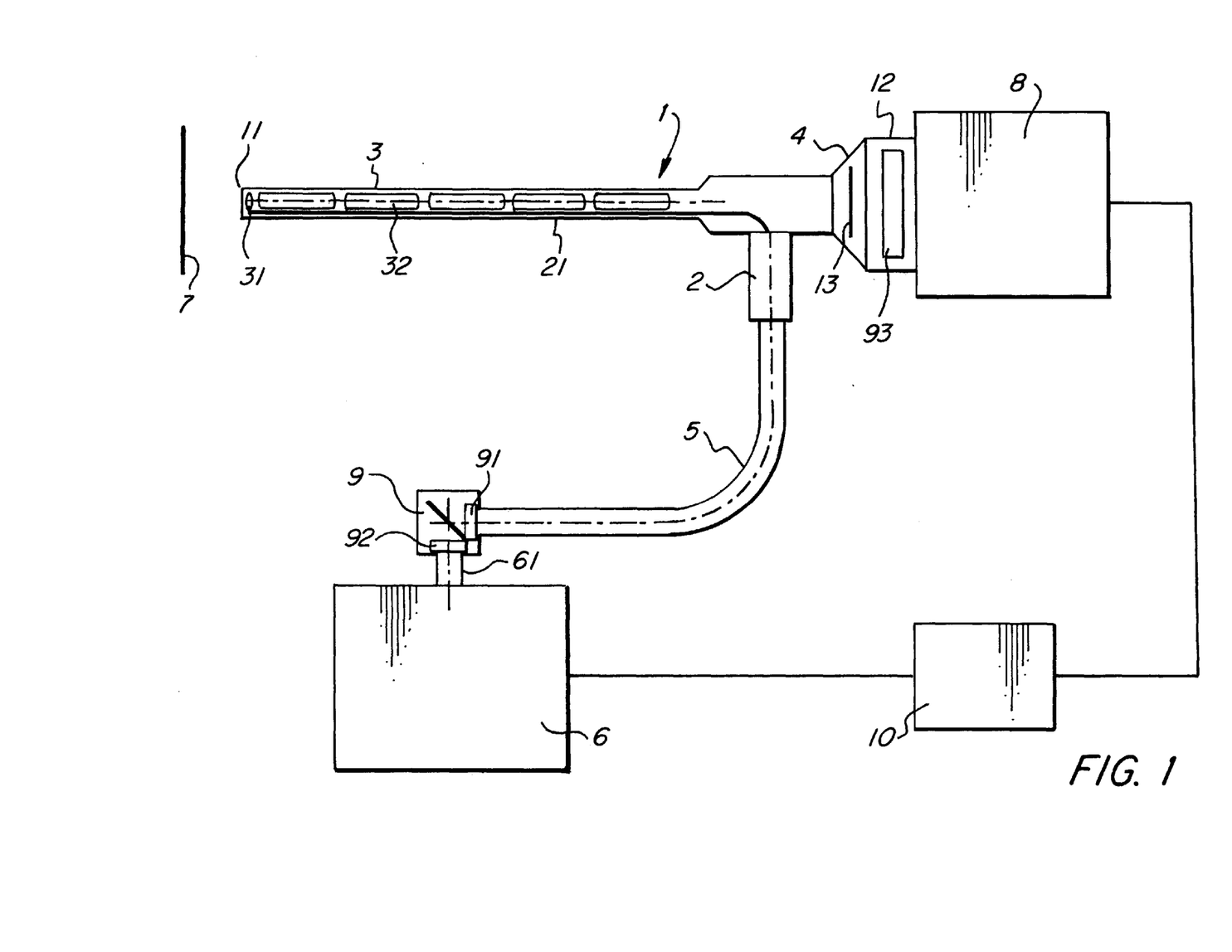
FIG. 1 schematically an invented device for endoscopic uses.

FIG. 1 shows schematically the design of an invented device for endoscopic uses. Reference number 1 stands for an endoscope which is provided in a known manner with a light conductor connection 2, a rod-shaped part 3, which can be introduced into a (not depicted) human body and an eyepiece 4.

The light conductor connection 2 is connected via a light conductor cable 5 to a light source 6 which, by way of illustration, may be provided with a xenon discharge lamp. A light conductor 21 in the endoscope 1, which conductor is composed for instance of a fiber bundle, guides the light from the source 6 coupled into the light conductor connection 2 to the distal end 11 of the endoscope 1. The light leaving the distal end 11 illuminates the to-be-examined tissue area 7.

The light coming from the tissue area 7 enters an objective 31, only schematically depicted, is guided via an image transmitter 32 to the proximal end 12 of the endoscope 1.

In the shown preferred embodiment, the image transmitter 32 is provided with a multiplicity of relay lens systems of which each executes a 1:1 image and is composed of so-called rod lens systems. Alternatively, the image transmitter 32 can be provided with a fiber imaging system.

The image of the tissue area 7 generated in the proximal image plane 13 can be observed through the eyepiece 4 with the eye. Alternatively or in addition to observation with the eye, the image can be recorded with a video camera 8 via a beam splitter. In the alternative shown in FIG. 1, the video camera 8 is directly attached to the eyepiece 4.

In as far as the design is described in the preceding, it is known from, by way of illustration, an endoscope provided with a video camera from Karl Storz GmbH & Co, Tuttlingen, Germany. For the details of the design, reference is made to this manufacturer's known endoscopes.

For conducting so-called photodynamic diagnoses, the device shown in FIG. 1 is improved to such an extent that filter systems can be placed in the illumination beam path and in the observation beam path.

For this purpose, in the preferred embodiment shown in FIG. 1, a filter system 9, to which the light conductor cable 5 is flanged, is attached to the light emergence connection 61 of light source 6. The filter system 9 is provided with a thermostable interference filter 91 and a thermostable heat protection filter 92, which is essentially supposed to reduce the thermal load of the interference filter 91. A filter 93 is also placed before the video camera 8 or the eye, with which the image is to be visually evaluated.

The exposure setting of the video camera 8 and the light emitted by the light source 6 is controlled by a control and evaluation unit 10. By way of illustration, the control and evaluation unit 10 can synchronize a flash-light source with the light integration phase of a CCD chip in the video camera 8. Furthermore, the control and evaluation unit 10 regulates the light power input emitted by the light source 6 and/or the exposure setting of the video camera.

Furthermore, the output signal of the video camera 8 is applied to the control and evaluation unit 10. The evaluation unit can, in particular, be provided with an image processing system which processes the output signal of the video camera further in the manner described in the introduction and represents the image-processed output signal on a monitor. Of course, the output signal emitted directly by the video camera and/or the image-processed output signal can also be stored, e.g. by means of a video recorder and/or stored in an image data bank or further processed in another manner by means of electronic data processing.

If a photosensibilisator is used, reflected illumination light as well as fluorescence light, caused by the light-induced reaction of the photosensibilisator in biological systems, is emitted by the tissue area 7. In order to be able to detect the, compared to the reflected light, small amount of fluorescence light and, in particular, to separate it from "non-fluorescence light" in subsequent image processing, a suitably selected transmission characteristic of the illumination beam path and observation beam path is required. Filters 91 and 93 placed in the beam path serve to set the transmission characteristic during the photodynamic diagnosis. As the filters, by way of illustration, can be removed by being swung out of the beam paths, normal observation of the tissue area 7 is also possible without, by way of illustration, leading to color distortion.

In the following, the characteristics of filters 91 and 93 for the first preferred embodiment of the present invention are described with reference to FIG. 2 for the event that delta amino levulinic acid is employed as the photosensiblisator. If other photosensibilisators are utilized, the filter characteristic has to be adapted accordingly.

Figure 2A:
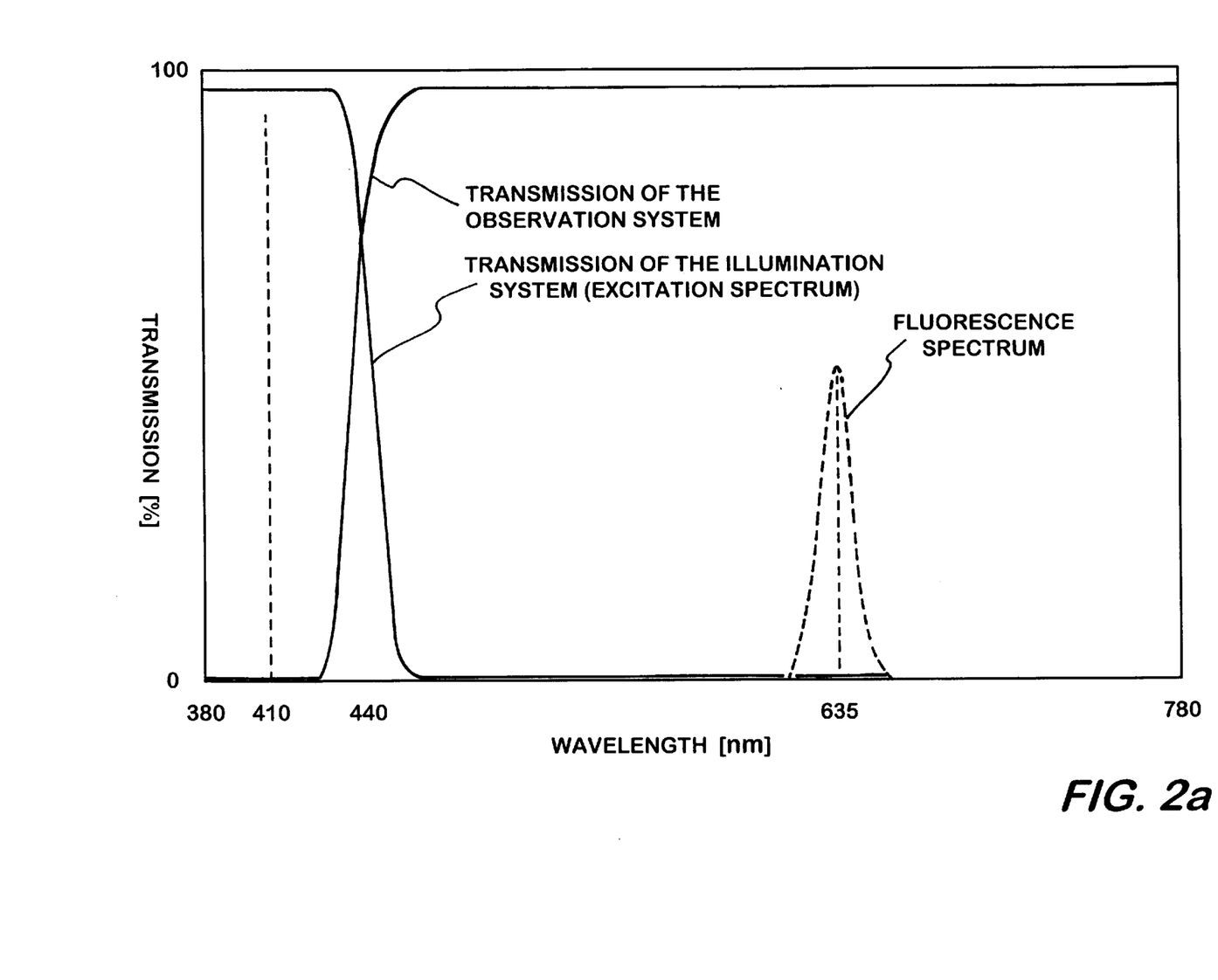
FIG. 2a the filter characteristic of the filters placed in the individual beam paths, FIG. 2b the "entire transmission" of a first preferred embodiment, and FIGS. 3a and b corresponding representations of a second preferred embodiment.

In FIG. 2a, the bold curve represents the transmission (in percent) of filter 91 as the function of the wavelength (in nm), thus the so-called net transmittance $T_i(\lambda)$, whereas the thin curve represents the net transmittance $T_i(\lambda)$ of filter 93. Furthermore, the fluorescence spectrum is plotted in FIG. 2a.

FIG. 2a shows the net transmission of filter 91 at wavelengths smaller than approximately 440 nm is greater than 90%. At wavelengths greater than approximately 460 nm, transmission is less than 1%. At about 455 nm, transmission is 50%. Furthermore, in the preferred embodiment of an interference filter 91, shown in FIG. 2a, transmission occurs in the range between 600 and 660 nm, preferably however 720 to 780 nm, in which the fluorescence light occurs more intensively, is especially low and, in particular, less than 0.1%, preferably 0.01%. Thus, filter 91 is a short pass filter.

Filter 93 has an almost opposite characteristic:

At wavelengths between 370 and 430 nm, transmission $T_i(\lambda)$ is less than 0.1% preferably even at least one magnitude less than 0.1%. At a wavelength of 445 nm, the transmission is 50%. At the wavelengths between 500 and 1100, the transmission is almost 99% or more.

The transmission curves of filters 91 and 93 intersect in the shown preferred embodiment approximately at transmission values of more than 60%. However, the curves may, and in particular preferably at weak fluorescence, also intersect at transmission values of 25 to 30%.

Figure 2B:
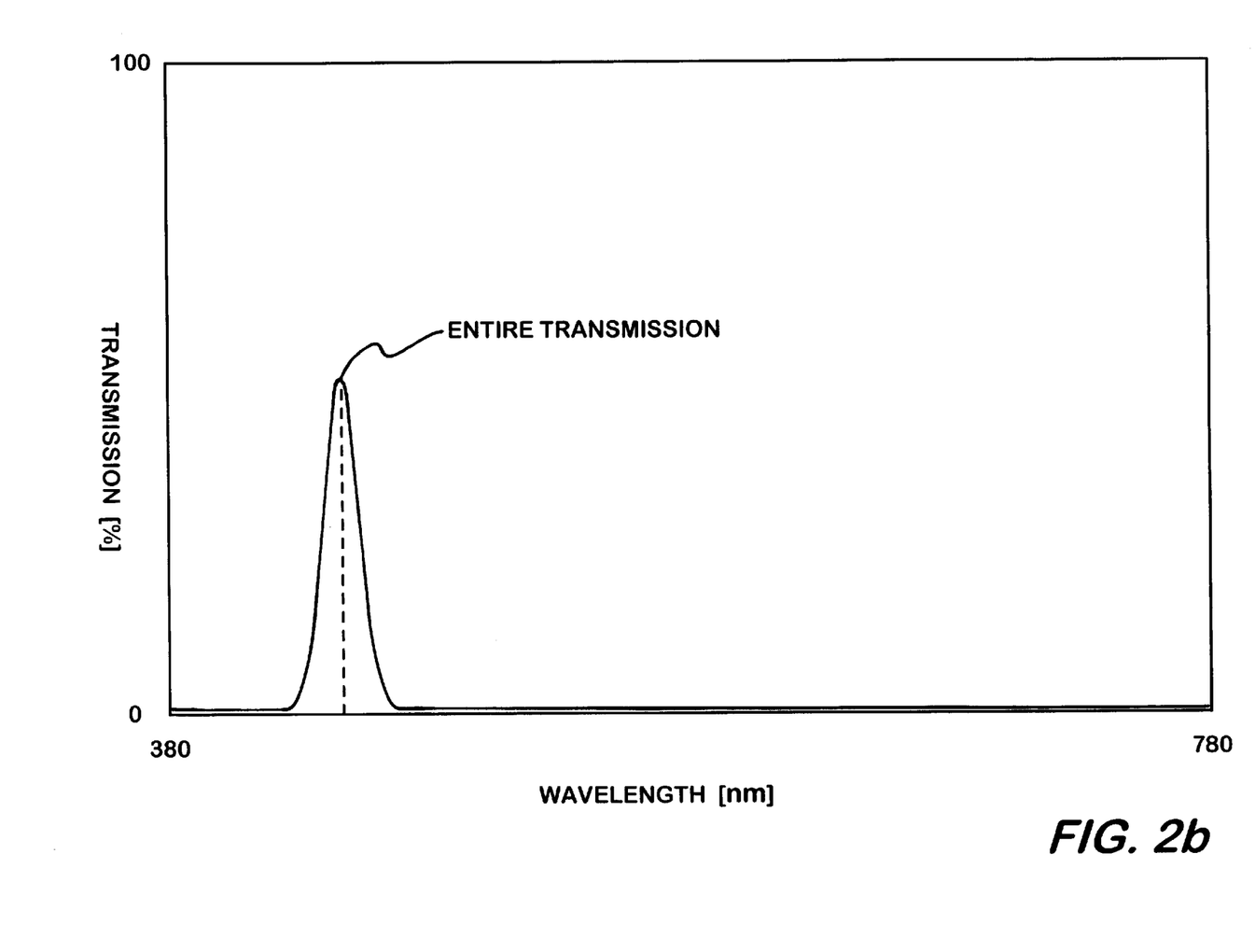

FIG. 2b shows the transmission characteristic of the entire system yielded by the multiplication of the curves of the individual filters 91 and 93. As can be seen, transmission lies above 1% only in the range between 440 and 460 nm and attains a maximum value of approximately 50%.

In the aforedescribed alternative, in which the curves intersect at transmission values from 25 to 30%, the maximum value is approximately 12.5%. This means that only a small part of the illumination light reflected at the tissue area 7 "reaches" the proximal image plane 13. The fluorescence light generally emitted at wavelengths $\lambda$ between 500 and 780 nm usually between 600 and 660 nm, reaches the image plane 13 unimpeded, because it has to pass only the long pass filter 93 but not the short pass filter 91.

Although this still permits visual observation of the tissue area 7, the fluorescence part of the determined light can be reliably separated from the reflected, short-wave light.

Figure 3A:
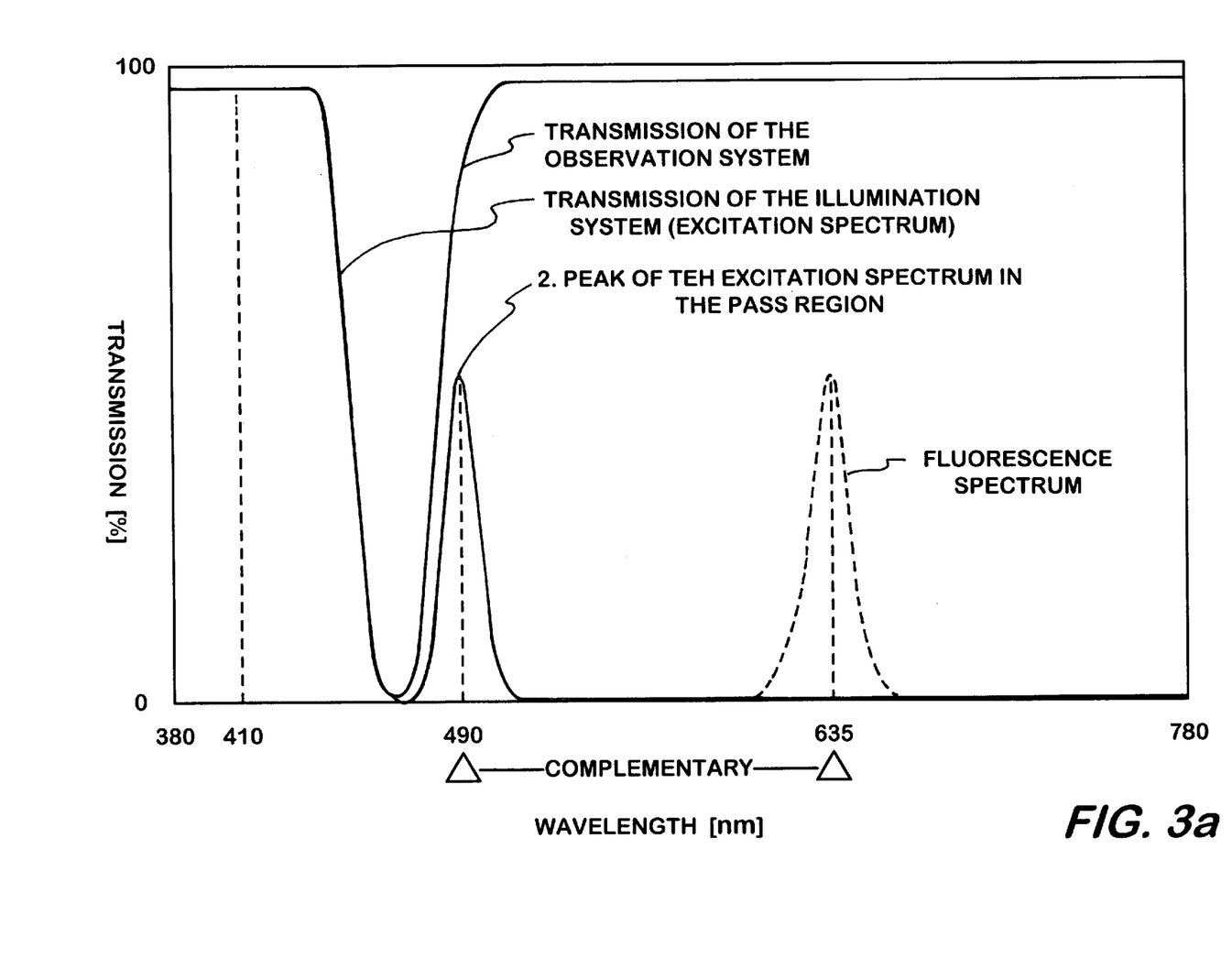
Figure 3B:
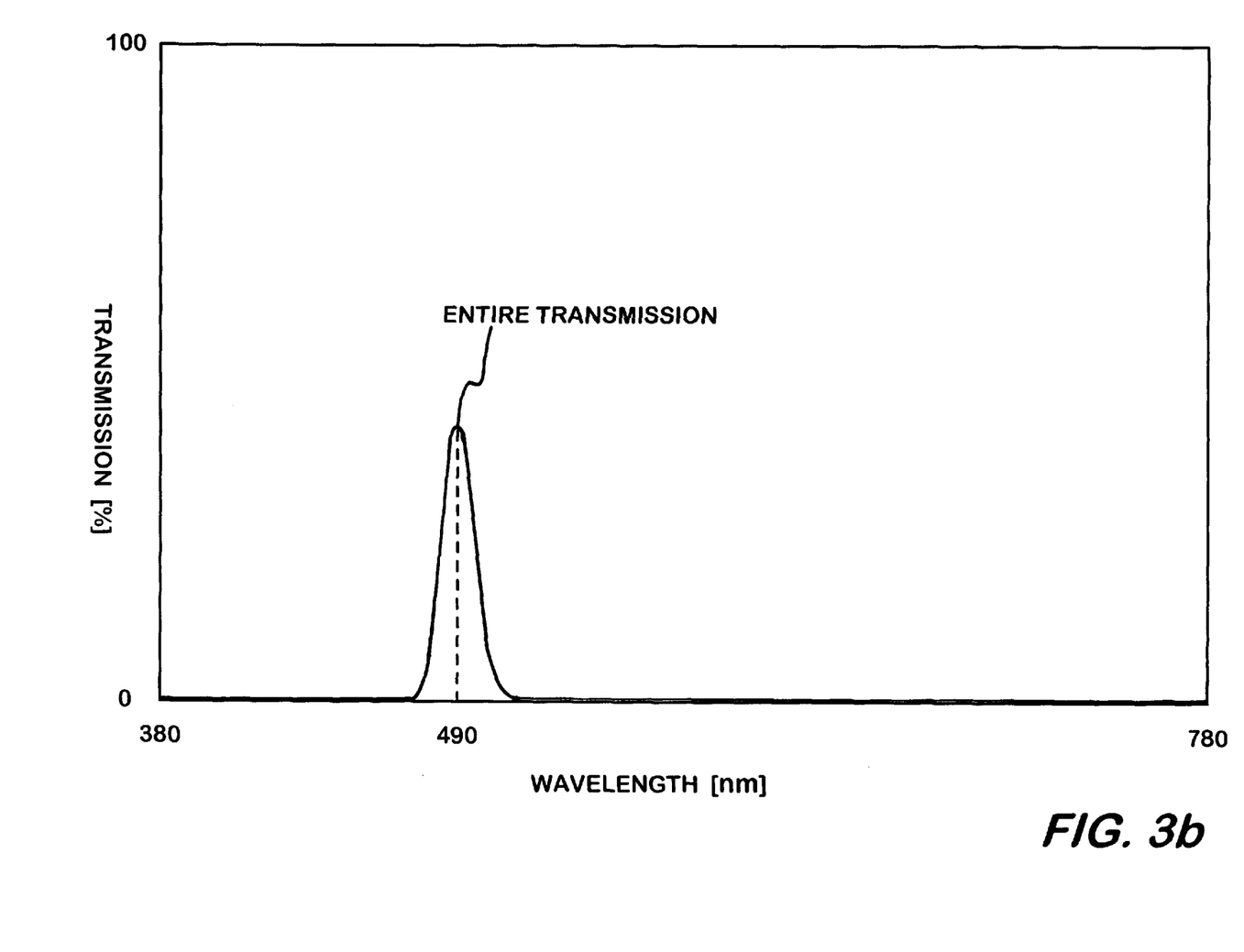

The FIGS. 3a and 3b show the corresponding curves of the second preferred embodiment of the present invention in which filter 91 placed in the illumination beam path as well as filter 93 placed in the observation beam path have a second pass region at approximately 490 nm±10 nm.

The wavelengths given in the preceding relate to the use of delta amino levulinic acid as the photosensibilator. If other photosensibilisators or if intrinsic fluorescence is utilized, the wavelengths, at which the individual filters change their transmission characteristics, have to be adapted accordingly. However, unaltered remains essentially the property that both complementary filter curves intersect at a net transmittance of approximately 50% or less than 50% or that there is a second pass region. Also unaltered remains that the entire system differs distinctly from zero and, in particular, is greater than 1% only in a small range, usually 50 nm if need be however more or less.

If the invented device is to be employed for therapy, the filter system 9 has to be provided with an additional filter which has no short pass characteristic but rather an intermediate pass to long pass characteristic.

The preceding description of preferred embodiments, which relates to the use of delta amino levulinic acid as the photosensibilisator, does not limit the scope or spirit of the overall inventive concept described in the claims or in the specification.

What is claimed is:

1. A device for "in vivo" diagnosis having
    an illumination system, which is provided with at least one light source having a lamp system (6) which generates incoherent light in a wavelength range of at least 380 to 680 nm,
    a light delivering unit (2,5,21) which directs the light of said illumination system at a to-be-diagnosed tissue area (7), and
    an imaging, image-recording and image-transmitting unit (31,32,4,8) which images light coming from said tissue area (7) in a proximal image plane (13), with a net spectral transmittance $T1(\lambda)$ of said light delivering unit being adapted to a fluorescence excitation spectrum of said tissue area,
    and a net spectral transmittance $Tb(\lambda)$ of said imaging unit being adapted to a fluorescence spectrum of said tissue area, and characterized by the fact that a net spectral transmittance of the device comprising said light delivering unit and said imaging unit possesses spectral transmittance of more than 5% only in a maximum wavelength range of about 50 nm.

2. A device according to claim 1, characterized by the fact that said illumination system is provided with a multiplicity of light sources of which one is a wide band light source having a lamp system and another is at least one laser system.

3. A device according to claim 2, characterized by the fact that all said light sources of said illumination system are coupled into said light delivering unit.

4. A device according to claim 1, characterized by the fact that transmission properties of said light transmitting unit and said imaging unit can be set by means of one or multiple optical elements.

5. A device according to claim 4 characterized by the fact that said transmission properties are set in such a manner that the overall intensity of the induced fluorescence light is of the same magnitude as the overall intensity of the part of the light of said illumination system reflected at the tissue area.

6. A device according to claim 4, characterized by the fact that said optical elements are filter systems (9,91,92,93) which can be placed in the illumination beam path respectively in the observation beam path.

7. A device according to claim 6, characterized by the fact that said filter system which can be placed in said illumination beam path and said filter system, which can be placed in said observation beam path possess an almost complementary filter characteristic.

8. A device according to claim 7 in conjunction with claim 1, characterized by the fact that the two complementary filter curves intersect at a net transmittance of the individual systems of less than 50%.

9. A device according to claim 7, characterized by the fact that said thermostable interference filter (91) is placed in said illumination beam path only for conducting the diagnosis procedure.

10. A device according to claim 6, characterized by the fact that said filter system in said illumination beam path is provided with at least two filters which can be placed in said beam path of which one said filters is a thermostable interference filter (91) and the other said filter is a thermostable heat protection filter (92) and, in particular, an interference filter.

11. A device according to claim 10, characterized by the fact that if delta amino levulinic acid is utilized as said photosensibilisator, said thermostable interference filter (91) possesses the following transmission properties in the visible range:

T1($\lambda$=380–430 nm)>50%

T1($\lambda$=610–650 nm)<1%, preferably <0.01%.

12. A device according to claim 11, characterized by the fact that the blocking factor of said thermostable interference filter (91) at a wavelength $\lambda$ of 630 nm with reference to the transmission maximum in the pass region at a wavelength of approximately 407 nm is greater than 1000.

13. A device according to claim 11 conjunction with claim 1, characterized by the fact that said thermostable interference filter (short pass filter 91) possesses the following characteristic:

T1($\lambda$=370–440 nm)>95%

T1($\lambda$=447 nm)=50%,

T1($\lambda$=460–600 nm)<1%

T1($\lambda$=600–660 nm)<0.1%,

T1($\lambda$=660–680 nm)<1%.

14. A device according to claim 13, characterized by the fact that the tolerance of the wavelength at which the transmission is 50% is ±2 nm.

15. A device according to claim 11 conjunction with claim 1, characterized by the fact that said thermostable interference filter (short pass filter 91) possesses the following characteristic:

T1($\lambda$=370–440 nm)>95%

T1($\lambda$=447 nm)=50%,

T1($\lambda$=460–480 nm)<1%

T1($\lambda$=490 nm)>10% and, in particular >30%

T1($\lambda$=500–600 nm)<1%

T1($\lambda$=600–660 nm)<0.1%,

T1($\lambda$=660–680 nm)<1%.

16. A device according to claim 11, characterized by the fact that said thermostable heat protection filter (92) possesses the following characteristic:

T1($\lambda$=380–440 nm)>95%

T1($\lambda$=440–700 nm)<90%,

T1($\lambda$=700 nm)=50%

T1($\lambda$=720–1100 nm)<1%.

17. A device according to claim 6, characterized by the fact that removal of said filters (91,92,93) from said beam paths is only possible if a monitoring signal enables the same.

18. A device according to claim 6, characterized by the fact that the carrier material if said filter system is quartz.

19. A device according to claim 1, characterized by the fact that the light source (6) is provided with at least one gas discharge lamp.

20. A device according to claim 19, characterized by the fact that said gas discharge lamp is a xenon gas discharge lamp.

21. A device according to claim 1, characterized by the fact that said light delivering unit is provided with a light conductor (21) having at least one fiber, whose numerical aperture is greater than 0.45.

22. A device according to claim 21, characterized by the fact that the core material of said fiber is composed of quartz and the encasing of a thermostable material.

23. A device according to claim 21, characterized by the fact that said gas discharge lamp of said illumination system is provided with a focal spot having a diameter of less than 2 mm and an elliptical reflector provided with a numerical aperture for light emergence of more than 0.45.

24. A device according to claim 21, characterized by the fact that said gas discharge lamp of said illumination system is provided with a focal spot having a diameter of less than 2 mm and a parabolic reflector as well as a focusing unit provided with a lens system having at least one aspherical surface.

25. A device according to claim 1, characterized by the fact that said illumination system is designed in such a manner that the excitation wavelengths are variable.

26. A device according to claim 1, characterized by the fact that a video unit (8) is disposed in said image plane.

27. A device according to claim 26, characterized by the fact that said video unit (8) is provided with a CCD image recorder, and that said gas discharge lamp (6) is a periodically operating flash discharge lamp, the flash exposure phase of which a control and evaluation unit (10) regulates in such a manner that the flash exposure occurs solely in the light integration phase of said CCD recorder.

28. A device according to claim 27, characterized by the fact that said illumination system is provided, in addition, with a continuously operating light source.

29. A device according to claim 26, characterized by the fact that said video unit is provided with a variable exposure setting.

30. A device according to claim 26, characterized by the fact that the output signal of said video unit is applied to an image processing system (10).

31. A device according to claim 30, characterized by the fact that said image processing system fades out a color tone range in the depicted color image.

32. A device according to claim 31, characterized by the fact that in the event of RGB processing said image processing system switches the blue and/or green channel on and off for contrast enhancement.

33. A device according to claim 31, characterized by the fact that said image processing system fades in the faded out color tone range shutterlike in the depicted color image.

34. A device according to 31, characterized by the fact that said image processing system is designed in such a manner that it conducts a HSI transformation.

35. A device according to one claim 31, characterized by the fact that said image processing system is designed in such a manner that in order to determine possible tumors, it calculates the contrast value at individual points of the image for the maximum fluorescence wavelength.

36. A device according to claim 35, characterized by the fact that if delta amino levulinic acid is utilized as the photosensibilisator, said image processing system calculates the contrast ratio for the wavelength 630 nm to the intensity in the range of maximum 50 nm, in which said entire system has a spectral transmittance of more than 5%.

37. A device according to claim 1, characterized by the fact that said light delivering unit and said imaging unit are integrated in a microscope.

38. A device according to claim 37, characterized by the fact that said microscope is a microscope for neurological or opthalmological examination.

39. A device according to claim 1, characterized by the fact that said light delivering unit and said imaging unit are integrated in an endoscope.

40. A device according to claim 39, characterized by the fact that the active light-permeable overall cross section surface of said light delivering unit does not exceed 4 mm$^2$.

41. A device according to claim 39, characterized by the fact that said light source is a known endoscopic light source.

42. A device according to claim 41, characterized by the fact that the power input of said light source is at least 300 watts.

43. A device for "in vivo" diagnosis having an illumination system, which is provided with at least one light source, a light delivering unit (2,5,21) which directs the light of said illumination system at a to-be-diagnosed tissue area (7), and an imaging, image-recording and image-transmitting unit (31,32,4,8) which images light coming from said tissue area (7) in a proximal image plane (13), with a net spectral transmittance $Ti_1(\lambda)$ of said light delivering unit being provided with a first pass region, which is adapted to a fluorescence excitation spectrum of said tissue area, and with a second pass region, and a net spectral transmittance $Tb(\lambda)$ of said imaging unit being provided with a first pass region, which is adapted to a fluorescence spectrum of said tissue area, characterized by the fact that the net spectral transmittance $Ti_1(\lambda)$ of said light delivering unit is provided with a second pass region, a wavelength range of which lies between wavelengths of said fluorescence excitation spectrum and wavelengths of said fluorescence spectrum, that the net spectral transmittance $Tb(\lambda)$ of said imaging unit is provided with a second pass region, which lies in a same wavelength range as said second pass region of said light delivering unit, and with a net transmittance of the device comprising said light delivering unit and said imaging unit having a spectral transmittance of more than 5% in said wavelength range.

44. A device according to claim 43, characterized by the fact that said first and said second pass region of the imaging unit are approximately complementary.

45. A device according to claim 44, characterized by the fact that said net transmission of the entire system is greater than 5% only in the range between 430 and 460 nm, and reaches in said range a maximum value of not more than 15%.

46. A device according to claim 43, characterized by the fact that said illumination system is provided with a multiplicity of light sources of which one is a wide band light source having a lamp system and another is at least one laser system.

47. A device according to claim 46, characterized by the fact that all said light sources of said illumination system are coupled into said light delivering unit.

48. A device according to claim 43, characterized by the fact that transmission properties of said light transmitting unit and said imaging unit can be set by means of one or multiple optical elements.

49. A device according to claim 48 characterized by the fact that said transmission properties are set in such a manner that the overall intensity of the induced fluorescence light is of the same magnitude as the overall intensity of the part of the light of said illumination system reflected at the tissue area.

50. A device according to claim 48, characterized by the fact that said optical elements are filter systems (9,91,92,93) which can be placed in the illumination beam path respectively in the observation beam path.

51. A device according to claim 50, characterized by the fact that said filter system which can be placed in said illumination beam path and said filter system, which can be placed in said observation beam path possess an almost complementary filter characteristic.

52. A device according to claim 51 in conjunction with claim 1, characterized by the fact that the two complementary filter curves intersect at a net transmittance of the individual systems of less than 50%.

53. A device according to claim 51, characterized by the fact that said thermostable interference filter (91) is placed in said illumination beam path only for conducting the diagnosis procedure.

54. A device according to claim 50, characterized by the fact that said filter system in said illumination beam path is provided with at least two filters which can be placed in said beam path of which one said filters is a thermostable interference filter (91) and the other said filter is a thermostable heat protection filter (92) and, in particular, an interference filter.

55. A device according to claim 54, characterized by the fact that if delta amino levulinic acid is utilized as said photosensibilisator, said thermostable interference filter (91) possesses the following transmission properties in the visible range:

$T_f(\lambda=380–430$ nm$)>50\%$ $T_f(\lambda=610–650$ nm$)<1\%$, preferably $<0.01\%$.

56. A device according to claim 55, characterized by the fact that the blocking factor of said thermostable interference filter (91) at a wavelength $\lambda$ of 630 nm with reference to the transmission maximum in the pass region at a wavelength of approximately 407 nm is greater than 1000.

57. A device according to claim 55 in conjunction with claim 43, characterized by the fact that said thermostable interference filter (short pass filter 91) possesses the following characteristic:

$T1(\lambda=370–440$ nm$)>95\%$ $T1(\lambda=447$ nm$)=50\%$, $T1(\lambda=460–480$ nm$)<1\%$ $T1(\lambda=490$ nm$)>10\%$ and, in particular $>30\%$ $T1(\lambda=500–600$ nm$)<1\%$ $T1(\lambda=600–660$ nm$)<0.1\%$, $T1(\lambda=660–680$ nm$)<1\%$.

58. A device according to claim 55, characterized by the fact that the tolerance of the wavelength at which the transmission is 50% is ±2 nm.

59. A device according to claim 55, characterized by the fact that said thermostable heat protection filter (92) possesses the following characteristic:

$T1(\lambda=380–440$ nm$)>95\%$ $T1(\lambda=440–700$ nm$)<90\%$, $T1(\lambda=700$ nm$)=50\%$ $T1(\lambda=720–1100$ nm$)<1\%$.

60. A device according to claim 50, characterized by the fact that removal of said filters (91,92,93) from said beam paths is only possible if a monitoring signal enables the same.

61. A device according to claim 50, characterized by the fact that the carrier material of said filter system is quartz.

62. A device according to claim 43, characterized by the fact that the light source (6) is provided with at least one gas discharge lamp.

63. A device according to claim 62, characterized by the fact that said gas discharge lamp is a xenon gas discharge lamp.

64. A device according to claim 43, characterized by the fact that said light delivering unit is provided with a light conductor (21) having at least one fiber, whose numerical aperture is greater than 0.45.

65. A device according to claim 64, characterized by the fact that the core material of said fiber is composed of quartz and the encasing of a thermostable material.

66. A device according to claim 64, characterized by the fact that said gas discharge lamp of said illumination system is provided with a focal spot having a diameter of less than 2 mm and an elliptical reflector provided with a numerical aperture for light emergence of more than 0.45.

67. A device according to claim 64, characterized by the fact that said gas discharge lamp of said illumination system is provided with a focal spot having a diameter of less than 2 mm and a parabolic reflector as well as a focusing unit provided with a lens system having at least one aspherical surface.

68. A device according to claim 43, characterized by the fact that said illumination system is designed in such a manner that the excitation wavelengths are variable.

69. A device according to claim 43, characterized by the fact that a video unit (8) is disposed in said image plane.

70. A device according to claim 69, characterized by the fact that said video unit (8) is provided with a CCD image recorder, and that said gas discharge lamp (6) is a periodically operating flash discharge lamp, the flash exposure phase of which a control and evaluation unit (10) regulates in such a manner that the flash exposure occurs solely in the light integration phase of said CCD recorder.

71. A device according to claim 70, characterized by the fact that said illumination system is provided, in addition, with a continuously operating light source.

72. A device according to claim 69, characterized by the fact that said video unit is provided with a variable exposure setting.

73. A device according to claim 69, characterized by the fact that the output signal of said video unit is applied to an image processing system (10).

74. A device according to claim 73, characterized by the fact that said image processing system fades out a color tone range in the depicted color image.

75. A device according to claim 74, characterized by the fact that in the event of RGB processing said image processing system switches the blue and/or green channel on and off for contrast enhancement.

76. A device according to claim 74, characterized by the fact that said image processing system fades in the faded out color tone range shutterlike in the depicted color image.

77. A device according to claim 74, characterized by the fact that said image processing system is designed in such a manner that it conducts a HSI transformation.

78. A device according to one claim 74, characterized by the fact that said image processing system is designed in such a manner that in order to determine possible tumors, it calculates the contrast value at individual points of the image for the maximum fluorescence wavelength.

79. A device according to claim 78, characterized by the fact that if delta amino levulinic acid is utilized as the photosensibilisator, said image processing system calculates the contrast ratio for the wavelength 630 nm to the intensity in the range of maximum 50 nm, in which said entire system has a spectral transmittance of more than 5%.

80. A device according to claim 43, characterized by the fact that said light delivering unit and said imaging unit are integrated in a microscope.

81. A device according to claim 80, characterized by the fact that said microscope is a microscope for neurological or ophthalmological examination.

82. A device according to claim 43, characterized by the fact that said light delivering unit and said imaging unit are integrated in an endoscope.

83. A device according to claim 82, characterized by the fact that the active light-permeable overall cross section surface of said light delivering unit does not exceed 4 mm$^2$.

84. A device according to claim 82, characterized by the fact that said light source is a known endoscopic light source.

85. A device according to claim 84, characterized by the fact that the power input of said light source is at least 300 watts.

86. A device for in vivo diagnosis of tissue, comprising:
an illumination system,
a light delivering unit having a first net spectral transmittance which overlaps with a fluorescence excitation spectrum of the tissue, and
an imaging, image-recording and image transmitting unit having a second net spectral transmittance which overlaps with a fluorescence emission spectrum of the tissue, wherein
the first and second net spectral transmittances overlap with each other such that a fluorescence image and a direct image of the tissue are both observable.

* * * * *